United States Patent [19]

Dewire et al.

[11] Patent Number: 5,413,262
[45] Date of Patent: May 9, 1995

[54] LUMBAR SUPPORTING BELT

[75] Inventors: Robert J. Dewire, Naperville, Ill.; John D. Krueger, Fontana, Wis.

[73] Assignee: Sears Roebuck & Co., Hoffman Estates, Ill.

[21] Appl. No.: 58,396

[22] Filed: May 7, 1993

[51] Int. Cl.6 .................................................. A45F 5/00
[52] U.S. Cl. ........................................ 224/253; 2/338; 224/901; 224/259; 224/215; 224/211; 229/904
[58] Field of Search ............... 224/901, 904, 208, 204, 224/206, 211, 215, 216, 253, 259, 209; 2/44, 338, 321, DIG. 6, 312

[56] References Cited

U.S. PATENT DOCUMENTS

| | | |
|---|---|---|
| 1,600,027 | 9/1926 | Welsard ..................... 224/904 X |
| 1,723,147 | 8/1929 | Fourethier ................. 224/211 X |
| 1,776,864 | 9/1930 | Cameron . | 
| 2,149,803 | 3/1939 | Wight ........................... 224/259 |
| 2,282,021 | 5/1942 | Benningfield .................. 128/100 |
| 3,089,143 | 5/1963 | Jacobson .................. 224/259 X |
| 3,101,718 | 8/1963 | Rocker . |
| 3,521,623 | 7/1970 | Nichols et al. . |
| 3,603,316 | 9/1971 | Lehman . |
| 3,664,560 | 5/1972 | Perkins ........................ 2/338 X |
| 3,754,549 | 8/1973 | Nelkin . |
| 4,029,243 | 6/1977 | Zerobnick et al. ............. 224/901 X |
| 4,099,524 | 7/1978 | Cueman et al. . |
| 4,545,370 | 10/1985 | Welsh . |
| 4,572,167 | 2/1986 | Brunswick ..................... 2/44 X |
| 4,782,535 | 11/1988 | Yewerth et al. ................... 2/321 |
| 4,819,846 | 4/1989 | Hannemann .................. 224/901 X |
| 4,836,194 | 6/1989 | Sebastian et al. . |
| 4,923,105 | 5/1990 | Snyder ........................... 224/255 |
| 4,957,231 | 9/1990 | Kalisher .................... 224/253 X |
| 4,962,873 | 10/1990 | Schattel ....................... 224/226 |
| 4,964,401 | 10/1990 | Taigen ...................... 2/338 X |
| 5,040,524 | 8/1991 | Votel et al. . |
| 5,064,108 | 11/1991 | Headley ...................... 224/253 |
| 5,086,759 | 2/1992 | Buddingh ..................... 2/44 X |
| 5,147,261 | 9/1992 | Smith et al. ................... 2/338 X |
| 5,184,764 | 2/1993 | Orovan et al. ................. 224/215 |
| 5,188,586 | 2/1993 | Castel .............................. 2/44 |
| 5,224,637 | 7/1993 | Colombo ................... 224/208 X |
| 5,240,156 | 8/1993 | Sicotte et al. ................ 224/901 X |

Primary Examiner—Ernest G. Cusick
Attorney, Agent, or Firm—Marshall, O'Toole, Gerstein, Murray & Borun

[57] ABSTRACT

In order to prevent injury to the back, a lumbar supporting belt includes a relatively wide inner belt and a relatively narrow outer belt. The inner belt is adapted to extend about the waist of a person. It has a middle region adapted to be positioned in the lumbar region of the back and has opposing ends adapted to be placed in proximity to one another. The inner belt is formed of a soft, flexible material which can have its opposing ends releasably connected. The outer belt is also adapted to extend about the waist of a person. It overlies the inner belt and has opposing ends corresponding to the opposing ends of the inner belt which are adapted to be placed in proximity to one another. The outer belt is formed of a flexible, non-stretchable material which can have its opposing ends releasably connected. In addition, the lumbar supporting belt may have a tool pouch which is supported in position by at least the outer belt thereof.

19 Claims, 3 Drawing Sheets

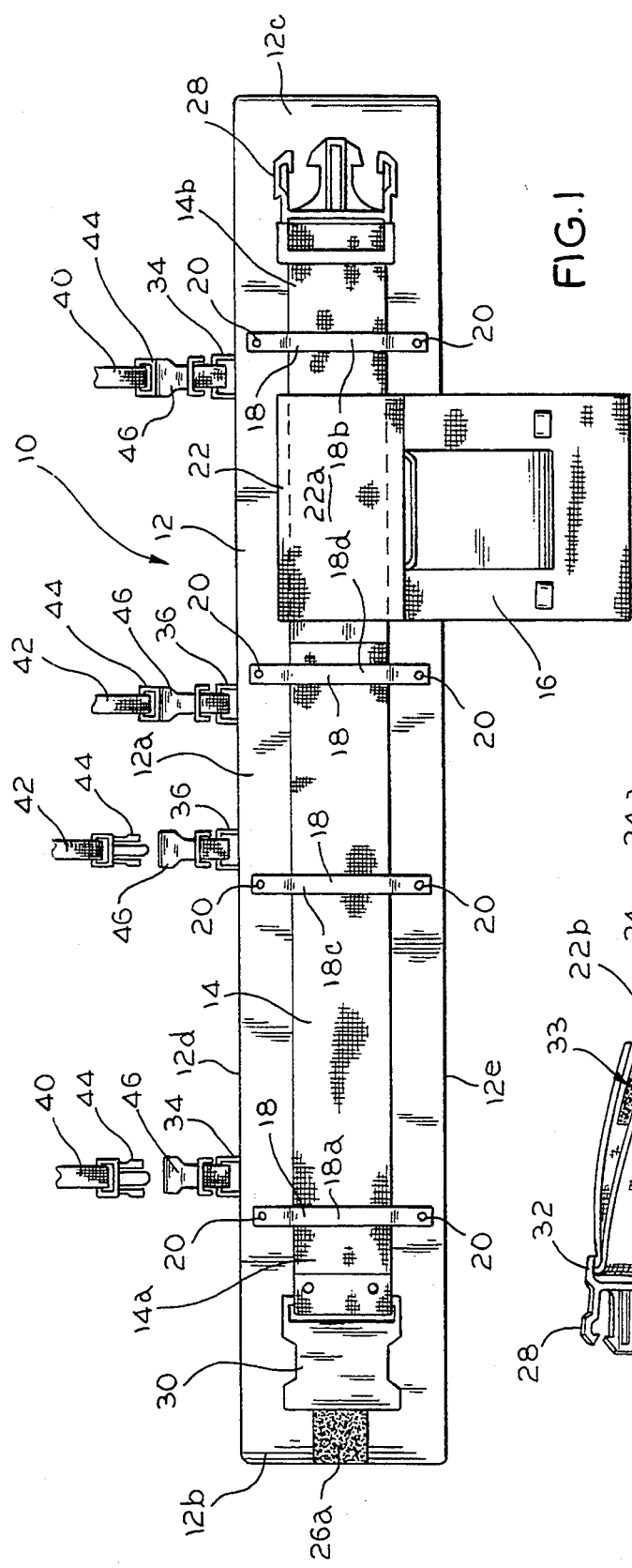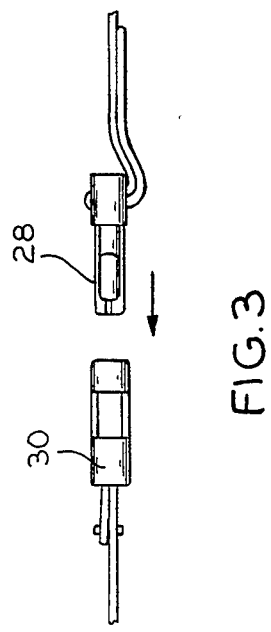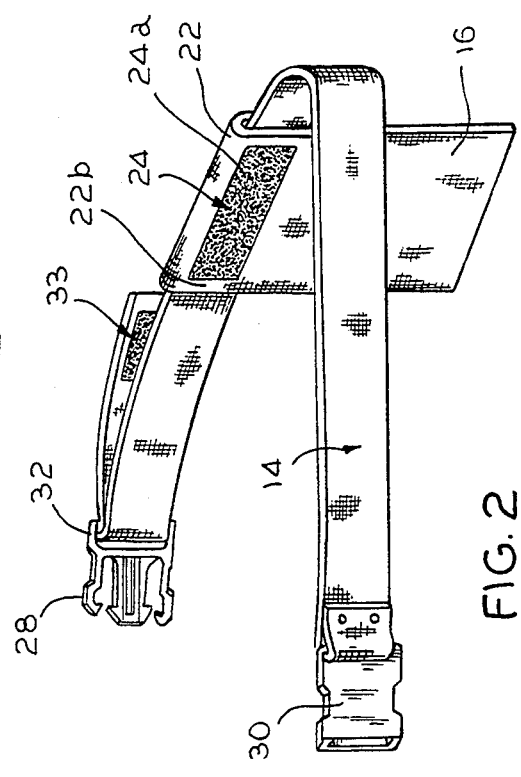

LUMBAR SUPPORTING BELT

FIELD OF THE INVENTION

The present invention is generally related to support belts and, more particularly, a belt that is lumbar supporting to reduce the risk of back injury.

BACKGROUND OF THE INVENTION

Over the years, there have been a wide variety of support belts, especially those commonly worn by carpenters, electricians and other workmen. These typically comprise a belt adapted to be worn around the waist and a tool pouch having a loop through which the belt extends. By way of example, it can be noted that such a belt is illustrated in Snyder U.S. Pat. No. 4,923,105, issued May 8, 1990.

Also, it is common knowledge that many workmen are particularly susceptible to back injury. This can result from a number of different sources such as the relatively heavy or awkward lifting, pulling or pushing that can and is often encountered. In addition, the weight of the tools that are typically carried by workmen is a constant strain on the back.

In view of the foregoing, there has been a continuing need for suitable equipment for the average workman. This equipment should ideally combine the multiple aspects of lumbar support and tool belt usage. If this was accomplished, workmen would then be able to function as required in a safer, more efficient and effective manner.

In addition, there has also been a recognized need for supporting the back during exercise of various types. These applications, of course, do not require a tool pouch or any other equivalent type of component to be support. Nevertheless, there has been a very real need for an improved lumbar supporting device in the field of exercise as well.

The present invention is directed to overcoming one or more of the foregoing problems and achieving one or more of the resulting objects.

SUMMARY OF THE INVENTION

It is, therefore, an object of the present invention to provide a belt which supports the lumbar region of the back. It is a further object of the present invention to provide such a belt wherein a tool pouch is supported by at least the outer one of a pair of belts. It is still an additional object of the present invention to provide selective rapid connection suspenders for such a belt.

Accordingly, the present invention is directed to a lumbar supporting belt comprising a wide inner belt and a narrower outer belt. The inner belt is adapted to extend about the waist of a person. It has a middle region adapted to be positioned in the lumbar region of the back and also has opposing ends adapted to be placed in proximity to one another. The inner belt is formed of a soft, flexible material. In addition to these features of construction, the belt further include means for releasably connecting the opposing ends of the inner belt.

Also, the outer belt is similarly adapted to extend about the waist of a person wearing the lumbar supporting belt. The outer belt is formed of a flexible, non-stretchable material which overlies the inner belt and has opposing ends corresponding to the opposing ends of the inner belt which are adapted to be placed in proximity to one another. With this arrangement, the belt still further includes means for releasably connecting the opposing ends of the outer belt.

Still additionally, the belt will accommodate any of a number of conventional tool pouches having a loop, and it is supported by at least the outer belt which preferably extends through the loop in relatively moveable relationship. The loop of the tool pouch advantageously has a front surface facing away from the inner belt and a rear surface facing toward the inner belt with the rear face having releasable support means thereon. When so constructed, it will be appreciated that the inner belt has a corresponding releasable support means positioned generally near one of the opposing ends and away from the middle region thereof.

In a preferred embodiment, the inner belt has a plurality of loops disposed on its outer surface in spaced relation to receive the outer belt therethrough. Each of these loops is advantageously permanently secured to the inner belt at two spaced points, one of which is generally adjacent a top edge and the other of which is generally adjacent a bottom edge of the inner belt in typical belt loop fashion. Preferably, the two spaced points where each of the loops is permanently secured are separated by a distance which is at least as great as the width of the outer belt.

More specifically, the inner belt preferably includes a first pair of loops which are positioned near the opposing ends of the inner belt. The outer belt is then advantageously of sufficient length that the opposing ends of the outer belt each extend through the first pair of loops by a distance sufficient to accommodate the releasable securing means. Still further, the inner belt also preferably includes a second pair of loops positioned inwardly of the first pair of loops generally toward the middle region of the inner belt. In a most highly preferred embodiment, the belt includes front and rear pairs of suspender connecting loops on the top edge of the inner belt. Then, an optional pair of suspenders having four loose ends is advantageously adapted to be releasably connected to the suspender connecting loops. For this purpose, the loose ends of the suspenders and the suspender connecting loops preferably have co-operable releasable connecting means.

Other objects, advantages and features of the present invention will become apparent from a consideration of the following specification taken in conjunction with the accompanying drawings.

IN THE DRAWINGS

FIG. 1 is a front elevational view of a lumbar supporting belt in accordance with the present invention;

FIG. 2 is a perspective view of an outer belt and tool pouch for the lumbar supporting belt of FIG. 1;

FIG. 3 is a side elevational view illustrating operation of the releasable connectors illustrated in FIG. 1;

DETAILED DESCRIPTION OF THE PREFERRED EMBODIMENT

Figure 4:
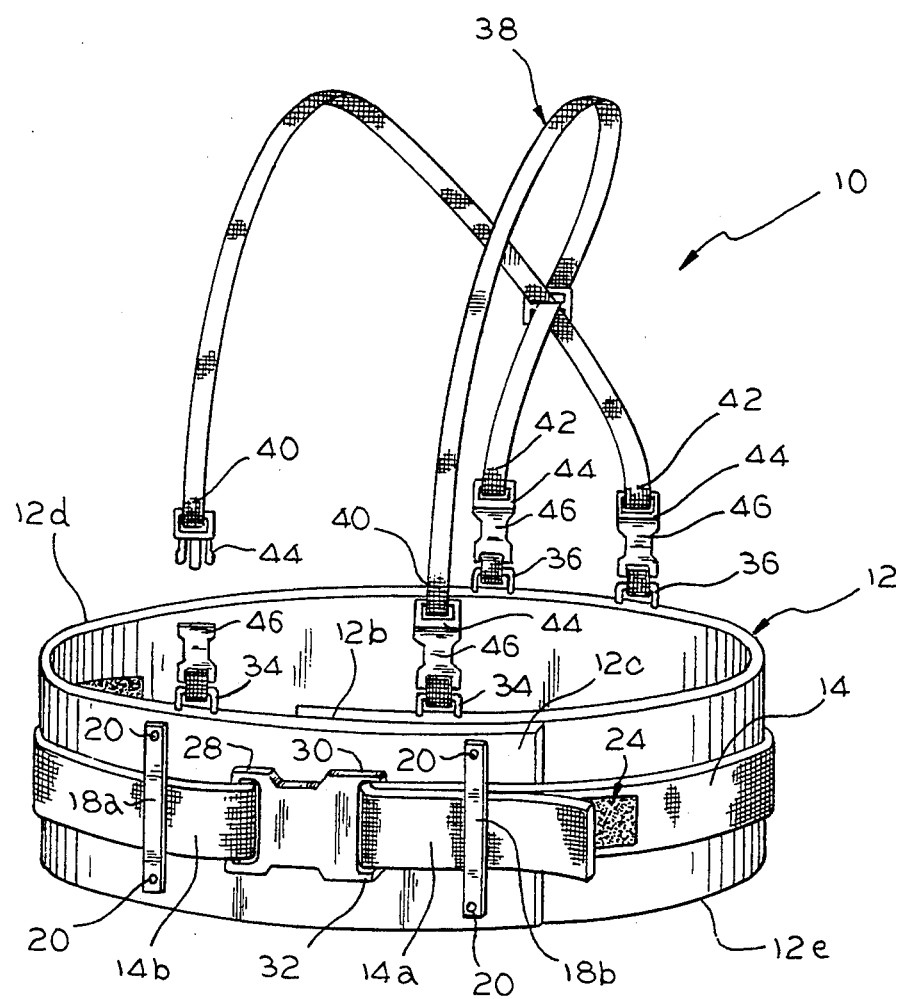
FIG. 4 is a perspective view of the lumbar supporting tool generally fastened and ready for use.

In the illustrations given, and with reference first to FIG. 1, the reference numeral 10 designates generally a lumbar supporting belt in accordance with the present invention. The belt 10 includes a relatively wide inner belt 12 and a relatively narrow outer belt 14, i.e., the inner belt 12 is quite wide relative to a normal belt and, in relation to the inner belt 12, the outer belt 14 is relative narrow (although it, too, is preferably wider than the typical belt used with slacks or the like). In addition, and as best shown in FIG. 1, the belt 10 will accommodate a tool pouch 16 supported by at least the outer belt 14 in a manner that will be described in greater detail hereinafter.

Referring now to FIGS. 1 and 4, the inner belt 12 is adapted to extend about the waist of a person. It will be seen that the inner belt 12 has a middle region 12a adapted to be positioned in the lumbar region of the back, and it also has opposing ends 12b and 12c adapted to be placed in proximity to one another. For this purpose, the inner belt 12 is advantageously formed of a soft, flexible material.

As will also be appreciated, the outer belt 14 is adapted to extend about the waist of a person. It will be seen that the outer belt 14 overlies the inner belt 12 and has opposing ends 14a and 14b corresponding to the opposing ends 12b and 12c, respectively, of the inner belt 12 which are similarly adapted to be placed in proximity to one another. For this purpose, it is advantageous for the outer belt 14 to be formed of a flexible, non-stretchable material.

As will be described hereinafter, the belt 10 includes means for releasably connecting the opposing ends 12b and 12c of the inner belt 12 to secure the inner belt 12 about the waist of the person after the inner belt 12 has been pulled tight with the middle region 12a in the lumbar region of the back. Also, and as will be described hereinafter, the belt 10 includes means for releasably connecting the opposing ends 14a and 14b of the outer belt 14 to secure the outer belt 14 about the waist of the person after the inner belt 12 has been pulled tight and the opposing ends 12b and 12c of the inner belt 12 have been connected.

As best shown in FIG. 1, the inner belt 12 has a plurality of loops 18 disposed in spaced relation to receive the outer belt 14 with each of the loops 18 being permanently secured to the inner belt 12. This is accomplished by means such as rivets 20, sewing or the like at two spaced points one of which is generally adjacent a top edge 12d and the other of which is generally adjacent a bottom edge 12e of the inner belt 12. As shown, the two spaced points where each of the loops 18 is permanently secured by means such as rivets 20 are generally separated by a distance which is at least as great as the width of the outer belt 14.

More specifically, and referring to FIG. 1, the inner belt 12 will be seen to include a first pair of loops 18a and 18b positioned near the opposing ends 12b and 12c of the inner belt 12. The outer belt 14 will be seen to be of sufficient length that the opposing ends 14a and 14b of the outer belt 14 each extend through the first pair of loops 18a and 18b by a distance sufficient to accommodate the releasable securing means that will be described in greater detail hereinafter. Also, as shown, the inner belt 12 includes a second pair of loops 18c and 18d positioned inwardly of the first pair of loops 18a and 18b generally toward and bridging the middle region 12a of the inner belt 12.

Referring specifically now to FIGS. 1 and 2, the tool pouch 16 will be understood to include a loop 22 through which the outer belt 14 extends in relatively movable relationship. The loop 22 of the tool pouch 16 (which may be any of a number of conventional pouches) has a front surface 22a facing away from the inner belt 12 (see FIG. 1) and a rear surface 22b facing toward the inner belt 12 (see FIG. 2) and the rear surface is supplemented to have releasable support means thereon as will be described in greater detail hereinafter. As will be appreciated, the inner belt 12 has a corresponding releasable support means positioned generally near one of the opposing ends such as 12c and away from the middle region 12a thereof.

Thus, and as best shown in FIG. 2, the inner belt 12 and the tool pouch 16 will have cooperating releasable support means disposed in generally confronting relation near one of the opposing ends such as 12c of the inner belt 12. The cooperating releasable support means includes a hook and loop fastener system generally designated 24 which is associated with the confronting surfaces of the inner belt 12 and the tool pouch 16. By way of example, the system 24 may comprise hook fastener portions 24a on the rear surface 22b of the tool pouch loop 22 and loop fastener portions (not shown) on the outwardly facing surface of the inner belt 12.

Figure 5:
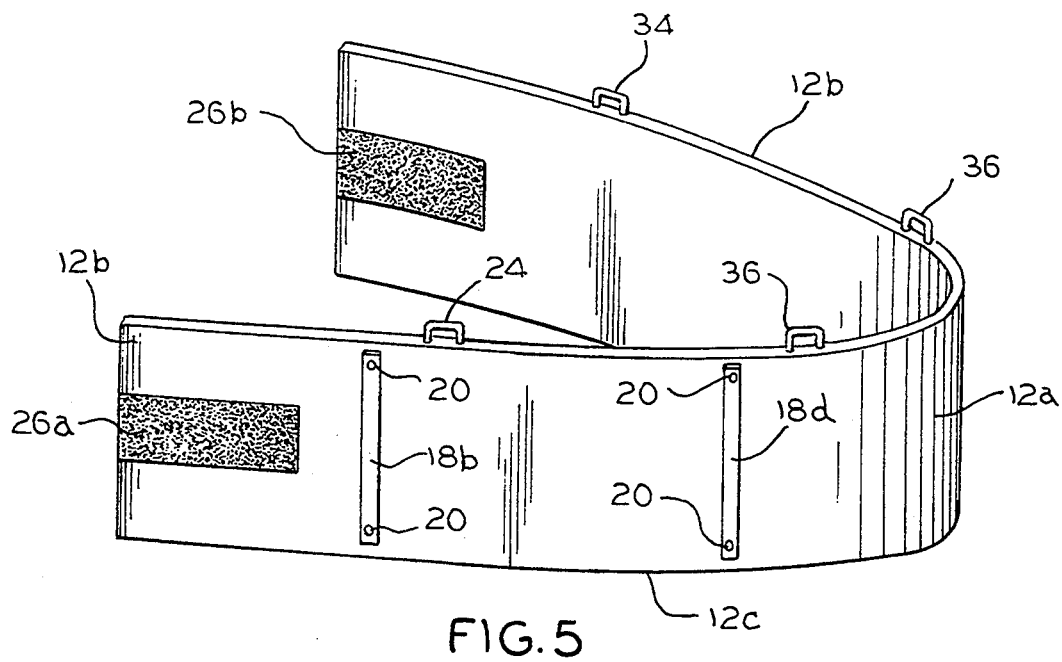
FIG. 5 is a perspective view of an inner belt for the lumbar supporting belt of FIG. 1.

Referring now to FIG. 5, the releasable connecting means for the opposing ends 12b and 12c of the inner belt 12 comprises a hook and loop fastener system which may, e.g., include a hook fastener portion 26a on the end 12b of the inner belt 12 and a loop fastener portion 26b on the end 12c of the inner belt 12. In this connection, the hook and loop fastener portions 26a and 26b may preferably take the form of the product sold under the trademark Velcro and it will be on opposite surfaces of the inner belt 12 so that the respective portions may be cooperatively engaged by overlapping the opposing ends 12b and 12c of the inner belt 12.

As best shown in FIG. 2, the releasable connecting means for the opposing ends 14a and 14b of the outer belt 14 comprises a quick release male and female connecter 28 and 30. It will be appreciated that either portion of the male and female connector 28 and 30 may be associated with either of the opposing ends 14a and 14b of the outer belt 14 as desired. In addition, at least one of the portions of the male and female connector 28 and 30 will preferably be formed to have an integral belt tightening means associated therewith.

In particular, and as shown in FIG. 2, the outer belt 14 preferably has a loose end associated with the connecter portion 28 which has been threaded through a typical loop arrangement 32. This loop arrangement 32 may be of a type conventionally utilized in connection with seat belts which, following connection of the male and female connecter 28 and 30, can be utilized by pulling on the loose end of the outer belt 14 to draw it tight about the waist of the person wearing the belt 10, although the outer belt 14 may also utilize any other type of integral belt tightening means. Furthermore, the outer belt 14 may have a hook and loop fastener system 33 including, e.g., a hook fastener portion 33a on the loose end of the outer belt 14 and a loop fastener portion (not shown) on the outwardly facing surface thereof.

With this arrangement, the loose end of the outer belt 14 may be secured to the outwardly facing surface thereof after it has been secured with the male and female connector 28 and 30 and tightened by pulling on the loose end of the outer belt 14 to prevent it from hanging loosely therefrom.

Referring now to FIGS. 1 and 4, the belt 10 includes front and rear pairs of suspender connecting loops or tabs 34 and 36 on the top edge 12d of the inner belt 12. A pair of suspenders 38 are provided having front and back loose ends 40 and 42 to be connected to the suspender connecting loops or tabs 34 and 36 respectively. As shown, the loose ends 40 and 42 of the suspenders 38 and the suspender connecting loops or tabs 34 and 36 advantageously have co-operable, releasable connecting means.

More specifically, the co-operable, releasable connecting means can take the form of a conventional snap-type of arrangement 44 and 46. It will be appreciated that such a snap connecter 44 or 46 will be associated with each of the suspender connecting loops or tabs 34 and 36 as well as each of the loose ends 40 and 42 of the suspenders 38. In this manner, the suspenders 38 may quickly and securely be releasably connected to the belt 10 as desired by, e.g., a workman.

With this feature, the suspenders 38 can be provided as an option that may not necessarily be originally purchased with the lumbar supporting belt 10. Thus, a workman can purchase the belt 10, either with or without a tool pouch such as 16, and, if it is later desired, purchase the suspenders 38 to assist in holding the belt 10 in any selected use position. In other words, the suspenders 38 can be utilized to help support the belt 10 against the weight of tools normally carried within the tool pouch 16.

As for the tool pouch 16, it will be appreciated that it can take any of a variety of different forms such as those known in the construction trades. It is only desirable that the tool pouch 16, whatever the form, have a loop such as 22 and, advantageously, a hook and loop fastener system such as that described above. With these features, the tool pouch 16 can be supported in a manner that does not cause sagging of the outer belt 14 even when it is fully loaded with tools.

Referring to FIGS. 1 and 5, the inner belt 12 will be seen to include a lumbar pad 50. This pad 50 may advantageously be made either as an integral portion of the inner belt 12 or as a separate pad that is secured thereto. Moreover, the exact size and construction of the lumbar pad 50 may be selected as desired.

Figure 6A:
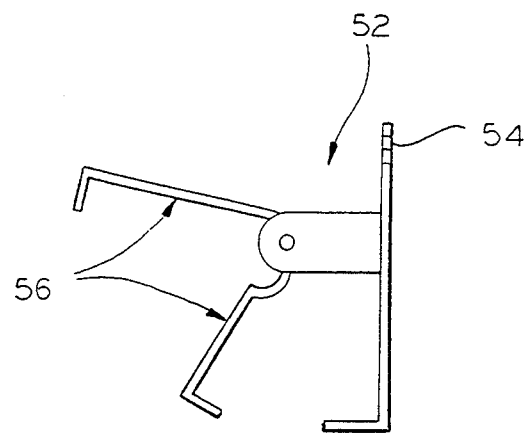
FIGS. 6a through 6c are side (open), side (closed), and front (closed) views of a clip for suspenders.
Figure 6B:
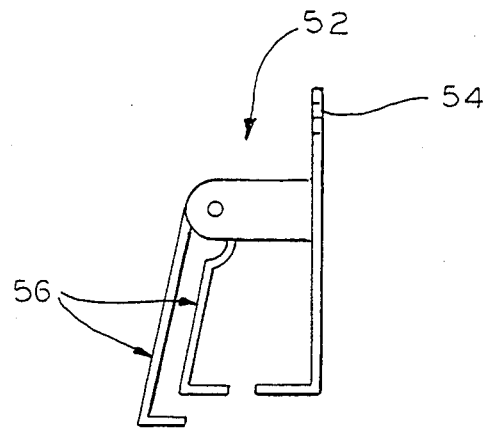
Figure 6C:
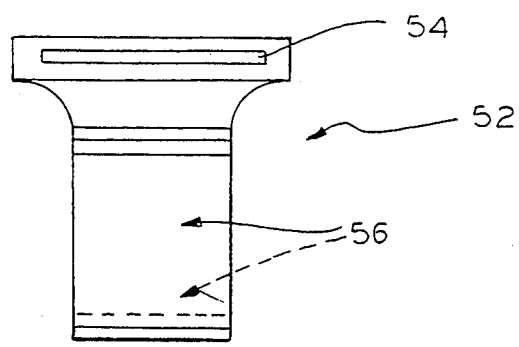

Finally, referring to FIGS. 6a through 6c, an alternative form of releasable connecting means is illustrated for the suspenders 38. The releasable connecting means illustrated comprises a clip generally designated 52 which has a slot as at 54 through which one of the loose ends such as 40 and 42 may be passed and following which that loose end may be doubled over upon the corresponding strap of the suspenders 38 to permanently secure the clip on the suspenders 38 as by sewing through the loose end and the strap. As shown, the clips 52 will also each have hinged locking arm arrangements 56 to cooperate with the suspender loops or tabs 34 and 36. While in the foregoing specification there has been set forth a preferred embodiment of the invention, it will be appreciated that the details herein given may be varied by those skilled in the art without departing from the true spirit and scope of the appended claims.

We claim:

1. A lumbar supporting belt, comprising:
   a relatively wide inner belt adapted to extend entirely about the waist of a person, said inner belt having a middle region adapted to be positioned in the lumbar region of the back and having opposing ends adapted to be placed in proximity to one another, said inner belt being formed of a soft, flexible material;
   means for releasably connecting said opposing ends of said inner belt to secure said inner belt about the waist of said person after said inner belt has been pulled tight with said middle region in the lumbar region of the back;
   a relatively narrow outer belt adapted to extend entirely about the waist of a person, said outer belt overlying said inner belt and having opposing ends corresponding to said opposing ends of said inner belt and adapted to be placed in proximity to one another, said outer belt being formed of a flexible, non-stretchable material;
   means for releasably connecting said opposing ends of said outer belt and tightening said outer belt to secure said outer belt tightly about the waist of said person after said inner belt has been stretched and said opposing ends of said inner belt have been connected;
   said outer belt being formed to have a sufficient length to extend entirely about said inner belt in relatively moveable relationship; and
   releasable support means on said inner belt for cooperation with corresponding releasably support means on a tool pouch when said releasably support means are disposed in generally confronting relationship, wherein the outer belt contributes to maintaining the cooperation of the releasable support means on said inner belt and said tool pouch.

2. The lumbar supporting belt of claim 1 wherein said inner belt has a plurality of loops disposed in spaced relation to receive said outer belt, each of said loops being permanently secured to said inner belt at two spaced points one of which is generally adjacent a top edge and the other of which is generally adjacent a bottom edge of said inner belt, said two spaced points where each of said loops is permanently secured to said inner belt being separated by a distance at least as great as the width of said outer belt.

3. The lumbar supporting belt of claim 1 wherein said inner belt includes a first pair of loops positioned near said opposing ends of said inner belt, said outer belt being of sufficient length that said opposing ends of said outer belt each extend through said first pair of loops by a distance sufficient to accommodate said releasable securing means, said inner belt also including a second pair of loops positioned inwardly of said first pair of loops generally toward said middle region of said inner belt.

4. The lumbar supporting belt of claim 1 including a tool pouch having a loop through which said outer belt extends in relatively movable relationship, said loop of said tool pouch having a front surface facing away from said inner belt and a rear surface facing toward said inner belt and said rear surface having releasable support means thereon, said inner belt having said corresponding releasable support means positioned generally near one of said opposing ends and away from said middle region thereof.

5. A lumbar supporting tool belt, comprising:
   a relatively wide inner belt adapted to extend entirely about the waist of a person, said inner belt having a middle region adapted to be positioned in the lumbar region of the back and having opposing ends adapted to be placed in proximity to one another, said inner belt being formed of a soft, flexible material;
   a plurality of spaced loops each of which is permanently secured to said inner belt at two spaced points one of which is generally adjacent a top edge and the other of which is generally adjacent a bottom edge of said inner belt;

means for releasably connecting said opposing ends of said inner belt to secure said inner belt about the waist of said person after said inner belt has been pulled tight with said middle region in the lumbar region of the back;

a relatively narrow outer belt adapted to extend entirely about the waist of a person, said outer belt overlying said inner belt and having opposing ends corresponding to said opposing ends of said inner belt and adapted to be placed in proximity to one another, said outer belt being formed of a flexible, non-stretchable material;

said outer belt being formed to have a sufficient length to extend through said loops and entirely about said inner belt in relatively movable relationship with said opposing ends positioned such that each can accommodate said releasable securing means;

means for releasably connecting said opposing ends of said outer belt and tightening said outer belt to secure said outer belt tightly about the waist of said person after said inner belt has been pulled tight and said opposing ends of said inner belt have been connected; and a tool pouch having a loop through which said outer belt extends in relatively movable relationship to support said tool pouch and a rear surface facing toward the inner belt;

said inner belt and said tool pouch having cooperating releasable support means said releasable support means of said pouch being positioned on said rear surface.

6. The lumbar supporting tool belt of claim 5 wherein said two spaced points where each of said loops is permanently secured to said inner belt is separated by a distance at least as great as the width of said outer belt.

7. The lumbar supporting tool belt of claim 5 wherein said plurality of spaced loops permanently secured to said inner belt include at least a pair of said loops positioned near said opposing ends of said inner belt.

8. The lumbar supporting tool belt of claim 5 wherein said plurality of spaced loops permanently secured to said inner belt include at least a pair of said loops positioned near said middle region of said inner belt.

9. The lumbar supporting tool belt of claim 5 wherein said loop on said tool pouch is formed to have a front surface facing generally away from said inner belt and the rear surface facing generally toward said inner belt.

10. The lumbar supporting tool belt of claim 5 wherein said cooperating releasable support means includes a hook and loop fastener system associated with confronting surfaces of said inner belt and said tool pouch.

11. A lumbar supporting tool belt, comprising:

a relatively wide inner belt adapted to extend entirely about the waist of a person, said inner belt having a middle region adapted to be positioned in the lumbar region of the back and having opposing ends adapted to be placed in proximity to one another, said inner belt being formed of a soft, flexible material;

a plurality of spaced loops each permanently secured to said inner belt at a point generally adjacent a top edge thereof and at a point generally adjacent a bottom edge thereof, said two points where each of said loops is permanently secured to said inner belt being separated by a distance equal to or greater than the width of said outer belt;

means for releasably connecting said opposing ends of said inner belt to secure said inner belt about the waist of said person after said inner belt has been stretched with said middle region in the lumbar region of the back;

a relatively narrow outer belt adapted to extend entirely about the waist of a person, said outer belt overlying said inner belt and having opposing ends corresponding to said opposing ends of said inner belt and adapted to be placed in proximity to one another, said outer belt being formed of a flexible, non-stretchable material;

said outer belt being formed to have a sufficient length to extend through said loops and entirely about said inner belt in relatively movable relationship with said opposing ends positioned such that each can accommodate said-releasable securing means means for releasably connecting said opposing ends of said outer belt and tightening said outer belt to secure said outer belt tightly about the waist of said person after said inner belt has been pulled fight and said opposing ends of said inner belt have been connected; and a tool pouch having a loop through which said outer belt extends in relatively movable relationship to support said tool pouch, said inner belt and said tool pouch have cooperating releasable support means near one of said opposing ends of said inner belt, said cooperating releasable support means including a hook and loop fastener system on confronting surfaces of said inner belt and said tool pouch.

12. The lumbar supporting tool belt of claim 11 wherein said plurality of spaced loops permanently secured to said inner belt include at least a pair of said loops positioned near said opposing ends of said inner belt and at least a pair of said loops positioned near said middle region of said inner belt but spaced to opposite sides thereof.

13. The lumbar supporting tool belt of claim 11 wherein said loop on said tool pouch is formed to have a rear surface facing generally toward said inner belt and said rear surface of said loop has one portion of said fastener system thereon with said confronting surface of said inner belt having the other portion of said fastener system thereon.

14. The lumbar supporting tool belt of claim 11 wherein said releasable connecting means for said opposing ends of said inner belt comprises a hook and loop fastener system and said releasable connecting means for said opposing ends of said outer belt comprises a quick release male and female connector having integral belt tightening means.

15. A lumbar supporting tool belt, comprising:

a relatively wide inner belt adapted to extend entirely about the waist of a person, said inner belt having a middle region adapted to be positioned in the lumbar region of the back and having opposing ends adapted to be placed in proximity to one another, said inner belt being formed of a soft, flexible material;

a plurality of spaced loops each permanently secured to said inner belt at a point generally adjacent a top edge thereof and at a point generally adjacent a bottom edge thereof, said two points where each of said loops is permanently secured to said inner belt being separated by a distance equal to or greater than the width of said outer belt;

said plurality of spaced loops permanently secured to said inner belt including at least a first pair of said loops positioned generally near said opposing ends of said inner belt and at least a second pair of said loops positioned generally near said middle region of said inner belt but spaced to opposite sides thereof;

means for releasably connecting said opposing ends of said inner belt to secure said inner belt about the waist of said person after said inner belt has been pulled fight with said middle region in the lumbar region of the back;

a relatively narrow outer belt adapted to extend entirely about the waist of a person, said outer belt overlying said inner belt and having opposing ends corresponding to said opposing ends of said inner belt and adapted to be placed in proximity to one another, said outer belt being formed of a flexible, non-stretchable material;

said outer belt being formed to have a sufficient length to extend through said loops and entirely about said inner belt in relatively movable relationship with said opposing ends positioned such that each can accommodate said releasable securing means means for releasably connecting said opposing ends of said outer belt and tightening said outer belt to secure said outer belt tightly about the waist of said person after said inner belt has been pulled tight and said opposing ends of said inner belt have been connected; and a tool pouch having a loop through which said outer belt extends in relatively movable relationship to support said tool pouch, said inner belt and said tool pouch have cooperating releasable support means near one of said opposing ends of said inner belt, said cooperating releasable support means including a hook and loop fastener system on confronting surfaces of said inner belt and said tool pouch;

said loop on said tool pouch being formed to have a rear surface facing generally toward said inner belt and said rear surface of said loop having one portion of said fastener system thereon with said confronting surface of said inner belt having the other portion of said fastener system thereon and said loop being of a length corresponding to the spacing between corresponding adjacent loops on said inner belt.

16. The lumbar supporting tool belt of claim 15 wherein said releasable connecting means for said opposing ends of said inner belt comprises a hook and loop fastener system and said releasable connecting means for said opposing ends of said outer belt comprises a quick release male and female connector having integral belt tightening means.

17. The lumbar supporting tool belt of claim 15 including front and rear pairs of suspender connecting loops on said top edge of said inner belt.

18. The lumbar supporting tool belt of claim 17 including a pair of suspenders having loose ends adapted to be connected to said suspender connecting loops.

19. The lumbar supporting tool belt of claim 18 wherein said loose ends of said suspenders and said suspender connecting loops have co-operable releasable connecting means.

* * * * *

UNITED STATES PATENT AND TRADEMARK OFFICE
CERTIFICATE OF CORRECTION

PATENT NO. : 5,413,262

DATED : May 9, 1995

INVENTOR(S) : Dewire et al.

It is certified that error appears in the above-identified patent and that said Letters Patent is hereby corrected as shown below:

column 8, line 24 replace "fight" with --tight--; and column 9, line 15 replace "fight" with --tight--.

Signed and Sealed this

Fifth Day of September, 1995

*Attest:*

BRUCE LEHMAN

*Attesting Officer*      *Commissioner of Patents and Trademarks*